(12) United States Patent
Bhandari et al.

(10) Patent No.: US 6,379,748 B1
(45) Date of Patent: Apr. 30, 2002

(54) TANTALUM AMIDE PRECURSORS FOR DEPOSITION OF TANTALUM NITRIDE ON A SUBSTRATE

(75) Inventors: Gautam Bhandari, Danbury; Thomas H. Baum, New Fairfield, both of CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 09/483,859

(22) Filed: Jan. 17, 2000

Related U.S. Application Data

(62) Division of application No. 09/012,679, filed on Jan. 23, 1998, now Pat. No. 6,015,917.

(51) Int. Cl.[7] .......................... C23C 14/06; C23C 14/14; C23C 14/48; H05H 1/24; H01L 21/443
(52) U.S. Cl. ............................... 427/255.394; 427/530; 427/531; 427/564; 427/576; 438/681; 438/653
(58) Field of Search .................................. 427/576, 564, 427/530, 531, 584, 255.394; 438/653, 681

(56) References Cited

U.S. PATENT DOCUMENTS

| | | | |
|---|---|---|---|
| 2,839,421 A | 6/1958 | Albisetti | 106/287.17 |
| 3,076,834 A | 2/1963 | Norton | 556/175 X |
| 3,288,829 A | 11/1966 | Wilkinson | 260/429 |
| 3,437,516 A | 4/1969 | Tamborski | 117/107.2 |
| 3,988,332 A | 10/1976 | Schrock | 260/429 R |
| 4,147,556 A | 4/1979 | Donley | 106/287.18 |
| 4,281,037 A | 7/1981 | Choung | 427/407.3 |
| 4,401,474 A | 8/1983 | Donley | 106/243 |
| 4,510,222 A | 4/1985 | Okunaka et al. | 430/5 |
| 4,529,427 A | 7/1985 | French | 65/3.12 |
| 4,726,938 A | 2/1988 | Rollat et al. | 423/DIG. 14 |
| 4,898,842 A | 2/1990 | David | 501/12 X |
| 4,908,065 A | 3/1990 | Tanitsu et al. | 106/287.19 X |
| 5,034,372 A | 7/1991 | Matsuno et al. | 505/1 |
| 5,110,622 A | 5/1992 | Hasegawa et al. | 427/126.1 |
| 5,120,703 A | 6/1992 | Snyder et al. | 505/1 |
| 5,165,960 A | 11/1992 | Platts | 427/166 |
| 5,204,314 A | 4/1993 | Kirlin et al. | 505/1 |
| 5,225,561 A | 7/1993 | Kirlin et al. | 546/256 |
| 5,280,012 A | 1/1994 | Kirlin et al. | 505/1 |
| 5,376,409 A | 12/1994 | Kaloyeros et al. | 427/248.1 |
| 5,412,129 A | 5/1995 | DiCarolis | 556/40 |
| 5,591,483 A | * 1/1997 | Winter et al. | 427/248.1 |
| 5,668,054 A | * 9/1997 | Sun et al. | 438/653 |
| 5,679,815 A | 10/1997 | Kirlin et al. | 556/42 |
| 5,711,816 A | 1/1998 | Kirlin et al. | 118/726 |

FOREIGN PATENT DOCUMENTS

| | | |
|---|---|---|
| DE | 3447635 A1 | 7/1985 |
| GB | 976573 | 11/1964 |

OTHER PUBLICATIONS

Yu. E. Ovchinnikov, et al. "The Crystal Structures of the Titanium–Containing Organosilicon Compounds $(SiMe_3)_3$ and $(SiMe_3)_3GeTi(Nme_2)_3$," Metallorg. Khim, (Organometallic Chem. In USSR), 1992, vol. 5, p. 564 no month.

Yu. E. Ovchinnikov Yu. T. Struchkov M. V. Ustinov, M.G. Voronkov, Crystal and Molecular Structure of Organosilicon Derivatives of Titanium (IV) $(Me_3Si)_3SiTi(Net_2)_3$ and CiTi $[N(SiMe_3)_2]_3$ Izu. Akad. Nauk SSSR, Ser. Khim., 1993, p. 1473 no month.

M.T. Bohr, "Scaling of High Performance Interconnects", Advanced Metallization and Interconnect Systems for ULSI Applications in 1996, MRS Publishers, 1997, p. 3 no month.

M.B. Small, D. Pearson, "On–Chip Wiring for VLSI Status and Directions", IBM J. Res. Dev., 1990, vol. 34, pp. 858–867 no month.

S. P. Muraka, R. J. Gutman, A. Kaloyeros and W. A. Lanford, "Advanced Multilayer Metallization Schemes with Copper as Interconnection Metal", Thin Solid Films, 1994, vol. 236, pp. 257–266 no month.

K. Holloway, et al., "Tantalum as a Diffusion Barrier Between Cooper and Silicon: Failure Mechanism and Effect of Nitrogen Additions," J. Appl. Phys., 1992 vol. 71, pp. 5433–5444 no month.

J.O. Olowolafe, C.J. Mogab, R.B. Gregory and M. Kottke, "Interdiffusions in Cu/Reactive–Ion–Sputtered TiN, Cu/Chemical–Vapor–Deposited TiN, Cu/TaN and TaN/Cu/TaN Thin–Film Structures: Low Temperature Diffusion Analyses", J. Appl. Phys., 1992, vol. 72, pp. 4099–4103 no month.

E. Kolawa, "Tantalum–Based Diffusion Barriers in Si/Cu VLSI Metallizations", J. Appl. Phys., 1991, vol. 70, pp. 1369–1373 no month.

S.–Q. Wang, et al., "Step Coverage Comparison of Ti/TiN Deposited by Collimated and Uncollimated Physical Vapor Depostion Techniques", J. Vac. Sci. Technol. B, 1996, vol. 14(3), pp. 1846–1852.

J.C. Fuggle et al, "Reactions of Niobium and Tantalum Pentafluorides with Trimethylsilyldiethylamine and with Trimethylsilyl Chloride", 1972, pp. 1766–1767 no month.

K. Hieber, "Structural and Electrical Properties of Ta and Ta Nitrides Deposited by Chemical Vapour Deposition", Thin Solid Films, 1974, vol. 24, pp. 157–164 no month.

(List continued on next page.)

Primary Examiner—Marianne Padgett
(74) Attorney, Agent, or Firm—Steven J. Hultquist; Margaret Chappuis

(57) ABSTRACT

Tantalum and titanium source reagents are described, including tantalum amide and tantalum silicon nitride precursors for the deposition of tantalum nitride material on a substrate by processes such as chemical vapor deposition, assisted chemical vapor deposition, ion implantation, molecular beam epitaxy and rapid thermal processing. The precursors may be employed to form diffusion barrier layers on microelectronic device structures enabling the use of copper metallization and ferroelectric thin films in device construction.

16 Claims, 4 Drawing Sheets

OTHER PUBLICATIONS

R. Fix, R. G. Gordon, D.M. Hoffman, "Chemical Vapor Deposition of Vanadium, Niobium, and Tantalum Nitride Thin Films", *Chem. Mater.,* 1993, vol. 5, pp. 614–619 no month.

D.N. Williams et al, "Half–sandwich Imido Complexes of Niobium and Tantalum", *J. Chem. Soc Dalton Trans.,* 1992, pp. 739–751 no month.

J. Li, T. E. Seidel, J. W. Mayer, "Copper–Based Metallization in ULSI Structures", *MRS Bulletin,* 1994, vol. XIX, No. 8, pp. 15–18.

S.M. Rossangle, et al., "Thin, High Atomicn Weight Refractory Film Deposition for Diffusion Barrier, Adhesion Layer, and Seed Layer Applications" *J. Vac. Sci. Technol. B,* vol. 14, pp. 1819–1827 no date.

D. Ugolini, S.P. Kowalczyk, F.R. McFeely, "Photoelectron Spectroscopy Studies of Chemical Vapor Deposition of Ta from a $TaF_6$ Precursor on Si and $SiO_2$ Substrates" *J. Appl. Phys.,* 1991, vol. 70, p. 3899 no month.

S.J. MaLain, et al., "Multiple Metal–Carbon Bonds. The Reaction of Niobium and Tantalum Neopentylidene Complexes with Simple Olefins: A Roule to Metallocyclopentanes", *J. Amer. Chem. Soc.,* 1977, vol. 99, p. 3519 no month.

R. R. Shrock, "Alkylidene Compexes of Niobium and Tantalum", *Acc. Chem. Res.,* 1979, vol. 12, p. 98 no month.

R. R. Schrock, S.M. Rockledge, "Tantalum Complexes Containing Diimido Bridging Dinitrogen Ligands" *J. Amer. Chem. Soc.,* 1980, vol. 102, pp. 7809–7811 no month.

Yuan–Wei Chao et al, "Preparation and Properties of Amido Halide Complexes of Niobium and Tantalum and Reactions with Alkynes", *Polyhedron,* 1990, vol. 9, No. 22, pp. 2709–2716 no month.

John D. Prostasiewicz, "Synthesis and Structural Characterization of Low Valent Group V Phosphine Complexes", *Inorg. Chem.,* 1992, vol. 31, pp. 4134–4142 no month.

D.C. Bradley et al, "Nuclear Magnetic Resonance Studies on Niobium and Tantalum Penta–alkoxides", *J. Chem. Soc. (A),* 1968, pp. 219–223 no month.

M.H. Tsai, S.C. Sun, C.P. Lee, H.T. Chiu, C.E. Tsai, S.H. Chuang, S.C. Wu, "Metal–Organic Chemical Vapor Deposition of Tantalum Nitride Barrier Layers for ULSI Applications", *Thin Solid Films,* 1995, vol. 270, pp. 531–536 no month.

H.T. Chiu, W.P. Chang, "Effect of Hydrogen on Deposition of Tantalum Nitride Thin Films From Ethylimidotantalum Complex", *J. Mater Sci. Lett.,* 1992, vol. 11, pp. 570–572 no month.

K. Sugiyama et al., "Low Temperature Deposition of Metal Nitrides by Thermal Decomposition of Organometallic Compounds", *J. Electrochem. Soc.,* 1975, vol. 122, p. 1545 no month.

M.G. Simmonds, W.L. Gladfelter, "Chemical Vapor Deposition of Aluminum", *The Chemistry of Metal CVD,* T.T. Kodas, M.J. Hampden–Smith, Eds., VCH, New York, 1994 no month.

T.D Tilley, *The Chemistry of Silicon Compounds,* S. Patai, Z. Rapporport Eds., Wiley: New York, 1989, vol. 2. p. 1415 no month.

Q. Jiang, P.J. Carroll, D. H. Berry, "Synthesis of Mono– and Bis(silyl) Complexes of Tantalum" *Organometallics,* 1991, vol. 10, pp. 3648–3655 no month.

"Diffusion Barriers of GaAs and InP Devices", *NASA, Tech Briefs,* Jun. 1997, p. 42.

"Adherent and Stable Metallization of CVD Diamond", *NASA Tech Briefs,* Jun. 1997, pp. 63–64.

M.F. Lappert, et al, *Metal and Metalloid Amides,* John Wiley and Sons, pp. 470–543 date no year.

R.P.M. Werner, A.H. Filbey, S.A. Manastyrsky, "Tetracarbonylcyclopentadienyl Compounds of the Group V Transition Metals", *Inorg. Chem.,* 1964, vol. 3, pp. 298–300 no month.

Z. Xue, L. Li, L. K. Hoyt, J.B. Diminnie, J.L. Pollitte, "Early Transition Metal Silyl Complexes Free from Anionic II–Ligands. A new Family of Alkyl, Alkylidene, and Alkylidyne Compounds", *J. Am. Chem. Soc.,* 1994, vol. 116, pp. 2169–2170 no month.

W.A. Nugent, R.L. Harlow, "Structure and Reactivity in the Group 5B t–Butylimido Complexes $(Me_2N)_3M=Nbu^t$; X–Ray Crystal and Molecular Structure of N–t–Butylimidotris(dimethylamido)tantalum", *J.C.S. Chem. Comm.,* 1978, pp. 579–580 no month.

A.A. Finn, L. Brandt, H.D. Kaesz, R.F. Hicks, "Chemical Vapor Deposition of Platinum, Palladium and Nickel", *The Chemistry of Metal CVD,* T.T. Kodas, M.J. Hampden–Smith, Eds., VCH, New York, 1994 no month.

Pradeep P. Phule, "Sol–gel Synthesis of Ferroelectric Lithium Tantalate Ceramics: FTIR Investigation of the Molecular Modification of Tantalum Ethoxide", *J. Mater. Res.,* 1993, vol. 8, No. 2, pp. 334–338 no month.

P.N. Kapoor et al, "Organic Compounds of Niobium and tantalum IV Reactions of Niobium and Tantalum Pentaethoxides with B–Diketones", *J. of the Less–Common Metals,* 1965, vol. 8., pp. 339–346 no month.

R.L. Deutsher, et al, "Eight Coordinate Tetrakis–Chelate Complexes of Niobium(IV) and Tantalum(V)", *Inorganica Chimica Acta,* 1970, pp. 645–650 no month.

R.R. Schrock et al, "Multiple Metal Carbon Bonds. Preparation and Characterization of Formation of the Tantalum and Niobium Neopentylidene Complexes M (CD2Cme3)3(CDCMe3)", J. Amer. Chem. Soc., 1978, vol. 100:11, pp. 3359–3370 no month.

Mark M. Bonaszak Holl, "Ladder Structure of $[(BuCH_2)_2TaN]5 \cdot NH_3 \cdot 2C_7H_8$ and Its relationship to Cubic TaN", *J. Am. Chem. Soc.,* 1990, vol. 112, pp. 7989–7994 no month.

Malcolm H. Chisolm, et al., "Chloro(dimethylamido) Compounds to Tantalum(V): Preparations, Properties, and Structures of $[Ta(NMe_2)_3Cl_2]$, $TaCl_3(NMe_2)_2$ $(HNMe_2)$, $Ta(NMe_2)_3Cl_2(HNMe_2)$, and $[TaCl_2(NMe_2)_2(HNMe_2)]_2O$" *Inorganic Chemistry,* 1981, vol. 20, pp. 1859–1865 no month.

H.–K. Shin, et al., "MOCVD of Titanium Nitride from a New Precursor, $Ti[N(CH_3)C_2H_5]_4$", *Chem. Mater.,* 1997, vol. 9, pp. 76–80 no month.

T. Kee, *Coordination Chemistry,* 1993, pp. 171–185 no month.

M. Stolz, K. Heiber, "Universal Chemical Vapour Depostion System for Metallurgical Coatings", *Thin Solid Films,* 1983, vol. 100, pp. 209–218 no month.

T. Don Tilley, "The Reactivity of Transition Metal–Silicon Compounds", Final Technical Report, Defense Technical Information Center, AD No. A200371, Aug. 8, 1988.

M.H. Tsai, S.C. Sun, C.P. Lee, H.T. Chiu, S.H. Chuang, "Metalorganic Chemical Vapor Deposition of Tungsten Nitride for Advanced Metallization", *Appl. Phys. Lett.,* 1996, vol. 68, pp. 1412–1414 no month.

M.H. Tsai, S.C. Sun, H.T. Chiu, C.E. Tsai, S.H. Chuang, "Metalorgaic Chemical Vapor Deposition of Tantalum Nitride by Tertbutylimidotris(diethylamido)tantalum for Advanced Metallization" *Appl. Phys. Lett.,* 1995, vol. 67, pp. 1128–1130 no month.

S.C.Sun et al, "Diffusion Barrier Properties of CVD Tantalum Nitride for Aluminum and Copper Interconnections", VMIC Conference, 1995 ISMIC, Jun. 27–29, pp. 157–161.

H.T. Chiu, S. H. Chuang, "Tungsten Nitride Thin Films Prepared by MOCVD", *J. Mater. Res.,* 1993, vol. 8, pp. 1353–1360 no month.

P. Catania, et al., "Low Resistivity Body–Centered Cubic Tantalum Thin Films as Diffusion Barriers Between Copper and Silicon", *J. Vac. Sci. Tech.,* A, 1992, A10 pp. 3318–3321 no month.

E. Blanquet, et al., "Evaluation of LPCVD Me–Si–N (Me= Ta, Ti, W, Re) Diffusion Barriers for Cu Metallizations", *Microelectronic Engineering,* 1997, vol. 37, pp. 189–195 no month.

Y.W. Chao, et al., "Preparation and Properties of Tantalum Imido Complexes and Their Reactions with Alkynes. Coordination Control through Multiple Metal–Ligand Bonding", *Inorg. Chem.,* 1989, vol. 28, pp. 3860–3868 no month.

M. M. Banaszak, et al., "Ammonolysis of Tantalum Alkyls: Formation of Cubic TaN and a Trimeric Nitride, [Cp*MeTaN]$_3$", *Inorg. Chem.* 1990, vol. 29, pp. 1518–1526 no month.

Zhang, J. et al., "Single Liquid Source Plasma–Enhanced Metalorganic Chemical Vapor deposition of High Quality YBa$_2$Cu$_3$O$_{7-x}$ Thin Films," Appl. Phys. Lett., 1992, vol. 61, pp. 2884–2886 no month.

Van Buskirk, P.C. et al., "MOCVD Growth of BaTiO$_3$ in an 8" Single–Wafer CVD System," Proc ISAF 92, Eighth Int'l Symp. Appl. Ferroelectrics, Agu. 31–Sep. 2, 1992. no month.

Hiskes, R. et al., "Single Source Metalorganic Chemical Vapor Deposition of Low Microwave Surface Resistance YBa$_2$Cu$_3$O$_7$," Appl. Phys. Lett. 1991, vol. 59, pp. 606–607 no month.

Zhang et al., "Plasma Enhanced Metalorganic Chemical Vapor Deposition of Conductive Oxide Electrodes for Ferroelectric BaTiO$_3$ Capacitors." Mater. Res. Soc. Symp. Proc. Vol. 310, pp. 249–254 (1993) no month.

Zhang et al., "Metal Organic Chemical Vapor Deposition of LaSrCoO Electrodes for Ferroelectric Capicitors," 6th ISAF Mtg., Mar., 1994.

T. Suzuki, "Comparison of CVD TiN, PECVD WN$_x$ and CVD W–Si–N as Upper Electrode Materials for Ta$_2$O$_5$ DRAM Capacitors", Advanced Metallization Conference, Sep. 28 1997, SanDiego.

S.Q. Wang, "Barriers Against Copper Diffusion into Silicon and Drift Through Silicon Dioxide", *MRS Bulletin,* Aug. 1994, pp. 30–40.

D.C. Bradley, M.H. Chisholm, "Transition Metal Dialkylamides and Disilylamides", *Accounts of Chemical Research,* 1976, vol. 9, pp. 273–280 no month.

S.–Q. Wang, et al., "Film Property Comparison of Ti/TiN Deposited by Collimated and Uncollimated Physical Vapor Deposition Techniques", *J. Vac. Sci. Technol. B,* 1996, vol. 14(3), pp. 1837–1845 no month.

F.W. Ainger, et al., "Deposition of Ferroelectric Oxides by MOCVD." *Prog. Crystal Growth Charact.,* 1991, vol. 22, pp. 183–187 no month.

Narula, et al., "Preparation and Characterization of Niobium(V) β–Diketonates", *Synth. React. Inorg. Met. Org. Chem,* 1983, vol. 13, pp. 1–19 no month.

Narula, et al., "Preparation and Characterization of Tantalum(V) β–Diketonates", *Synth. React. Inorg. Met. Org. Chem,* 1983, vol. 13, pp. 887–898 no month.

* cited by examiner

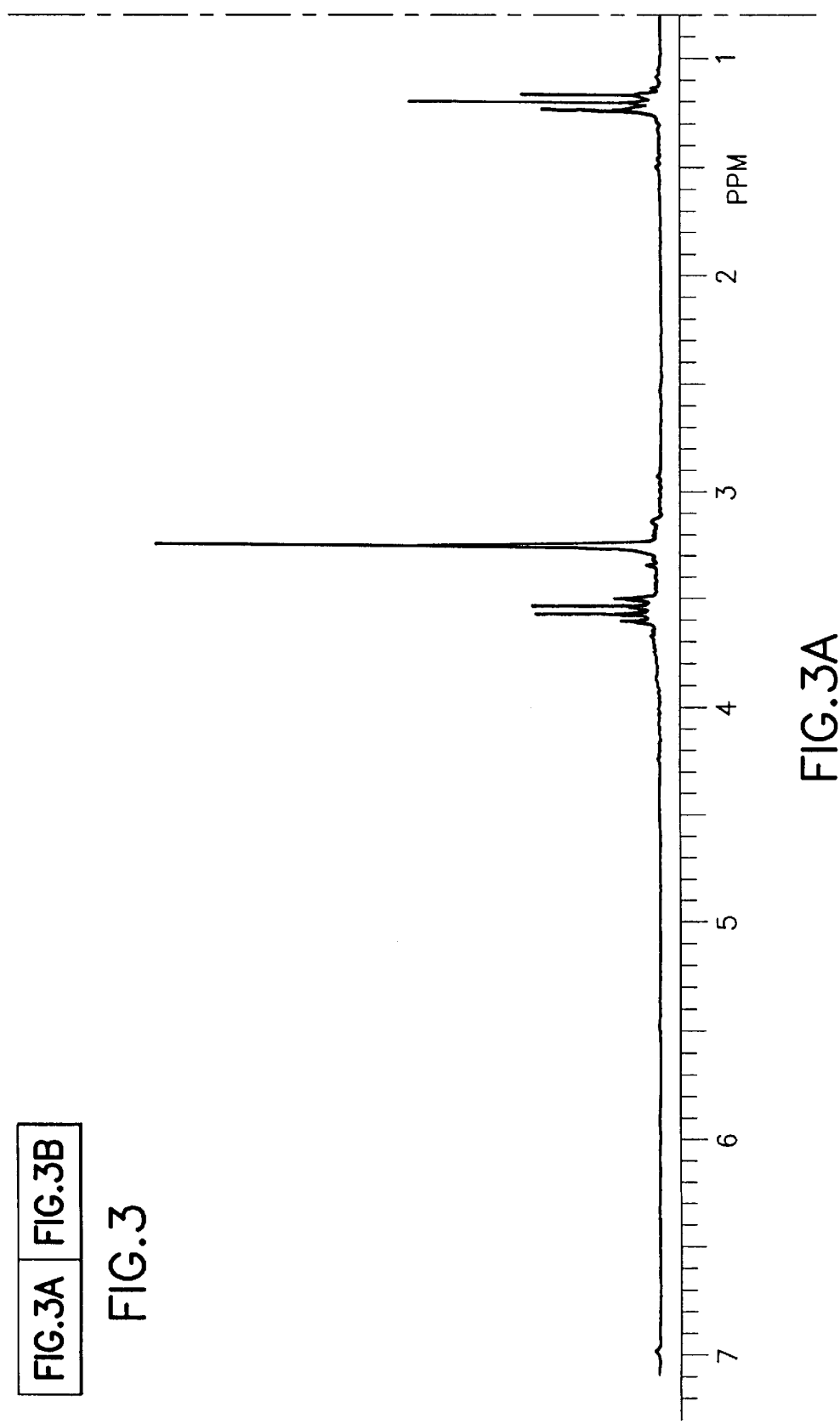

US 6,379,748 B1

TANTALUM AMIDE PRECURSORS FOR DEPOSITION OF TANTALUM NITRIDE ON A SUBSTRATE

This is a division of U.S. application Ser. No. 09/012,679 now U.S. Pat. No. 6,015,917 filed Jan. 23, 1998.

BACKGROUND OF THE INVENTION

1. Field of the Invention

The present invention relates to Ta and Ti precursors useful in the formation of a Ta-based or Ti-based material on a substrate, and includes tantalum amide precursors for formation of tantalum nitride on a substrate, and methods of use of such precursors for forming TaN material, e.g., thin film layers of TaN, on a substrate. The invention also contemplates single source compounds for the formation of TaSiN or TiSiN material on a substrate.

2. Description of the Related Art

Copper is of great interest for use in metallization of VLSI microelectronic devices because of its low resistivity, low contact resistance, and ability to enhance device performance (relative to aluminum metallization) via reduction of RC time delays thereby producing faster microelectronic devices. Copper CVD processes which are suitable for large-scale manufacturing and the conformal filling of high aspect ratio inter-level vias in high density integrated circuits are extremely valuable to the electronics industry, and are therefore being extensively investigated in the art.

Although CVD of Cu is gaining momentum in the semiconductor manufacturing industry, several problems still inhibit the integration of copper metallurgy in such microelectronic device applications. In specific, CVD of a suitable diffusion barrier for the copper metallization must be available to ensure the long-term reliability of the copper-based metallurgy in integrated circuits (ICs).

TaN and TaSiN have been demonstrated as a suitable metal diffusion barrier. A CVD process of TaN would obviously be advantageous and is currently the focus of development efforts by semiconductor equipment manufacturers. The CVD of TaN is at present carried out using $Ta(NMe_2)_5$, a solid source precursor, as the source reagent. However, $Ta(NMe_2)_5$ is a solid, and given the limited volatility of $Ta(NMe_2)_5$, new, robust and more volatile tantalum amide precursors are needed. The films deposited from such sources must be conducting, conformnal and of high purity. It would be extremely advantageous to utilize a suitable liquid source reagent as a tantalum amide precursor. For example, an alternative TaN precursor is $Ta(NEt_2)_5$, which is reportedly a liquid. However, this source reagent is unstable to elevated temperature conditions, readily decomposing to a tantalum imide species, $Ta(NEt)(NEt_2)_3$, upon heating, and thereby is an unsatisfactory candidate as a liquid source reagent for TaN barrier layer formation.

TaSiN and TiSiN are also currently being investigated in the art as diffusion barriers. A CVD process for these ternary barrier layer materials would also be advantageous and also is the focus of development efforts in the field. The CVD of TaSiN is at present carried out using $Ta(NMe2)_5$ as the Ta source and silane as the silicon source. Further, $TaCl_5$ in combination with silane and ammonia has been used to deposit TaSiN thin films. Apart from the hazards associated with handling a pyrophoric gas such as silane, the dual source reactor configuration required with such precursor species ($TaCl_5$, $Ta(NMe_2)_5$ and silane) also increases the cost and complexity of the semiconductor manufacturing operation.

Another approach to barrier layer formation entails the PVD or CVD deposition of high purity Ta metal on the silicon substrate. The resulting Ta layer will form $TaSi_x$ at the silicon contact region (i.e., the Ta bottom surface), and subsequent elevated temperature reaction of the Ta layer with a nitrogenous reactant such as $NH_3$ or $N_2$ will induce nitridation of the Ta top-surface. Thus, a TaSiN ternary diffusion barrier or a layered TaSi/TaN structure can be formed. This type of ternary diffusion barrier has been reported in the art and provides excellent contact resistance and diffusion barrier properties towards Cu metallization and integration of ferroelectric thin films.

In all instances of the formation of a Ta-based diffusion barrier, an effective CVD approach to conformally coat inter-level (<0.15 $\mu$m) vias and sidewalls is critical, and the CVD source reagent must be storage-stable, of appropriate volatility and vaporization characteristics, with good transport and deposition characteristics to produce a high-purity, electronic quality thin film.

There is a continuing and increasing need in the art for improved CVD source reagents for forming Ta-based diffusion barrier layers on microelectronic substrates, to facilitate copper metallization. Such CVD source reagents are desirably liquid in character, to facilitate their processibility using techniques such as liquid delivery CVD, wherein the liquid source reagent is rapidly vaporized, e.g., by flash vaporization on a heated element such as a grid, screen or porous metal body, to produce a volatilized source reagent. The resulting source reagent vapor can then be transported to the CVD chamber and contacted with a substrate maintained at appropriate elevated temperature, to effect the deposition on the substrate of the Ta-based material.

It therefore is an object of the present invention to provide useful precursor compositions for the formation of Ta-based material and Ti-based material on substrates.

It is another object of the invention to provide a method of forming a Ta-based material, such as TaN or TaSiN, or a Ti-based material, such as TiN or TiSiN, on a substrate, using such precursor compositions.

Other objects and advantages of the present invention will be more fully apparent from the ensuing disclosure and appended claims.

SUMMARY OF THE INVENTION

The present invention relates generally to tantalum and titanium source reagents for the formation of Ta-based and Ti-based materials on a substrate by techniques such as chemical vapor deposition, and in particular and preferred practice of the invention, liquid delivery chemical vapor deposition.

As used herein, the term "liquid delivery" when referred to chemical vapor deposition or other thin film or coating process refers to the fact that the precursor or source reagent composition for the material to be deposited on a substrate is vaporized from a liquid form to produce a corresponding precursor vapor which then is transported to the locus of deposition, to form the material film or coating on the substrate structure. The liquid phase which is vaporized to form the precursor vapor may comprise a liquid phase source reagent per se, or the source reagent may be dissolved in or mixed with a liquid to facilitate such vaporization to place the source reagent in the vapor phase for the deposition operation.

As used herein, the term "perfluoroalkyl" is intended to be broadly construed to include groups containing alkyl moieties which are partially or fully substituted in fluorine atoms, and thus perfluoroalkyl includes for example a trifluoroalkyl substituent whose alkyl moiety is $C_1$–$C_4$ alkyl, such as trifluoromethyl.

In one compositional aspect, the present invention relates to a precursor composition comprising at least one tantalum and/or titanium species selected from the group consisting of:

(i) tethered amine tantalum complexes of the formula:

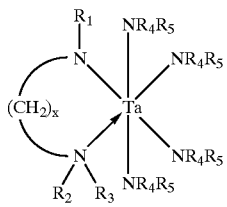

wherein:
  X is 2 or 3;
  each of $R_1$–$R_5$ is independently selected from the group consisting of H, $C_1$–$C_4$ alkyl, aryl (e.g., phenyl), $C_1$–$C_6$ perfluoroalkyl (e.g., a trifluoroalkyl substituent whose alkyl moiety is $C_1$–$C_4$ alkyl, such as trifluoromethyl), and trimethylsilyl;

(ii) β-diimines of the formula:

$TaG_xQ_{5-}$ wherein:
  G is a β-diimino ligand;
  each Q is selected from the group consisting of H, $C_1$–$C_6$ alkyl, aryl and $C_1$–$C_6$ perfluoroalkyl; and
  x is an integer from 1 to 4 inclusive;

(iii) tantalum diamide complexes of the formula

$Ta(N(R_1)(CH_2)_xN(R_2))_y(NR_3R_4)_{5-2y}$ wherein:
  x is 1 or 2;
  y is 1 or 2;
  each of $R_1$–$R_4$— is independently selected from the group consisting of H, $C_1$–$C_4$ alkyl, aryl, perfluoroalkyl, and trimethylsilyl;

(iv) tantalum amide compounds of the formula

$Ta(NRR')_5$ wherein each R and R' is independently selected from the group consisting of H, $C_1$–$C_4$ alkyl, phenyl, perfluoroalkyl, and trimethylsilyl, subject to the proviso that in each NRR' group, R R';

(v) β-ketoimines of the formula

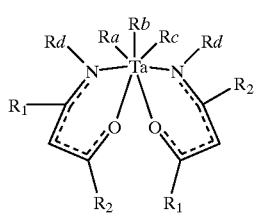

wherein each of $R_1$, $R_2$, $R_a$, $R_b$, $R_c$ and $R_d$ is independently selected from H, aryl, $C_1$–$C_6$ alkyl, and $C_1$–$C_6$ perfluoroalkyl; and (v) tantalum cyclopentadienyl compounds of the formula:

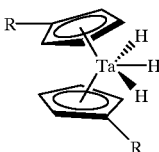

wherein each R is independently selected from the group consisting of H, methyl, ethyl, isopropyl, t-butyl, trimethylsilyl;

(vii) $Ta(NR_1R_2)_x(NR_3R_4)_{5-x}/Ti(NR_1R_2)_x(NR_3R_4)_{4-x}$ or $Ta(NR_1)(NR_2R_3)_3$ where each of $R_1$, $R_2$, $R_3$ and $R_4$ are independently selected from the group consisting of H, $C_1$–$C_8$ alkyl (e.g., Me, Et, $^t$Bu, $^i$Pr, etc.), aryl (e.g., phenyl), $C_1$–$C_8$ perfluoroalkyl (e.g., $CF_3$ or a fluoroalkyl whose alkyl moiety is $C_1$–$C_4$, such as trifluoromethyl), or a silicon-containing group such as silane ($SiH_3$), alkylsilane, (e.g., $SiMe_3$, $Si(Et)_3$, $Si(^iPr)_3$, $Si(^iPr)_3$, $Si(^tBu)_3$, perfluoroalkylsilyl (e.g., $Si(CF_3)_3$), triarylsilane (e.g., $Si(Ph)_3$), or alkylsilylsilane (e.g., $Si(SiMe_3)_x(Me)_{3-x}$);

(viii) $Ta(SiR_1R_2R_3)_x(NR_4R_5)_{5-x}/Ti(SiR_1R_2R_3)_x(NR_4R_5)_{4-x}$ where $R_{1-5}$ can any be combination of H, Me, Et, $^t$Bu, Ph, $^i$Pr, $CF_3$, $SiH_3$, $SiMe_3$, $Si(CF_3)_3$, $Si(Et)_3$, $Si(^iPr)_3$, $Si(^tBu)_3$, $Si(Ph)_3$, $Si(SiMe_3)_x(Me)_{3-x}$ and $Si(SiMe_3)_x(Me)_{3-x}$; and (ix) $(Cp'')Ta(SiR_1R_2R_3)_x(Cp'')_2Ti(SiR_1R_2R_3)(NR_4R_5)$ where $R_{1-5}$ can any be combination of H, Me, Et, $^t$Bu, Ph, $^i$Pr, $CF_3$, $SiH_3$, $SiMe_3$, $Si(CF_3)_3$, $Si(Et)_3$, $Si(^iPr)_3$, $Si(^tBu)_3$, $Si(Ph)_3$, $Si(SiMe_3)_x(Me)_{3-x}$ and $Cp''$ is $C_5H_xMe_{(5-x)}$ (where x=0–5).

In one aspect, the present invention relates to tantalum amide precursors for formation of tantalum nitride on a substrate, and to methods of forming TaN material on a substrate from such precursors, wherein the precursor composition comprises at least one tantalum species selected from the group consisting of:

(i) tethered amine tantalum complexes of the formula:

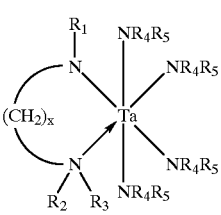

wherein:
  X is 2 or 3;
  each of $R_1$–$R_5$ is independently selected from the group consisting of H, $C_1$–$C_4$ alkyl, aryl (e.g., phenyl), $C_1$–$C_6$ perfluoroalkyl (e.g., a trifluoroalkyl substituent whose alkyl moiety is $C_1$–$C_4$ alkyl, such as trifluoromethyl), and trimethylsilyl;

(ii) β-diimines of the formula:

$TaG_xQ_{5-x}$ wherein:
  G is a β-diimino ligand;
  each Q is selected from the group consisting of H, $C_1$–$C_6$ alkyl, aryl and $C_1$–$C_6$ perfluoroalkyl; and x is an integer from 1 to 4 inclusive;
(iii) tantalum diamide complexes of the formula

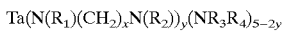

wherein:
  x is 1 or 2;
  y is 1 or 2;
  each of $R_1$–$R_4$— is independently selected from the group consisting of H, $C_1$–$C_4$ alkyl, aryl, perfluoroalkyl, and trimethylsilyl;
(iv) tantalum amide compounds of the formula

wherein each R and R' is independently selected from the group consisting of H, $C_1$–$C_4$ alkyl, phenyl, perfluoroalkyl, and trimethylsilyl, subject to the proviso that in each NRR' group, R R';
(v) β-ketoimines of the formula

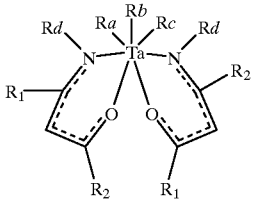

wherein each of $R_1$, $R_2$, $R_a$, $R_b$, $R_c$ and $R_d$ is independently selected from H, aryl, $C_1$–$C_6$ alkyl, and $C_1$–$C_6$ perfluoroalkyl; and
(vi) tantalum cyclopentadienyl compounds of the formula

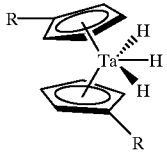

wherein each R is independently selected from the group consisting of H, methyl, ethyl, isopropyl, t-butyl, trimethylsilyl.
In another aspect, the present invention relates to a tantalum amide precursor composition for forming a tantalum nitride material on a substrate, including at least one tantalum amide species selected from the above-described selection group, and a solvent for such tantalum amide species. The solvent may be selected from the group consisting of $C_6$–$C_{10}$ alkanes, $C_6$–$C_{10}$ aromatics, and compatible mixtures thereof. Illustrative alkane species include hexane, heptane, octane, nonane and decane. Preferred alkane solvent species include $C_8$ and $C_{10}$ alkanes. Preferred aromatic solvent species include toluene and xylene. In the most preferred approach, no solvent is required to deliver the liquid source reagents.
In another aspect, the invention relates to a method of forming a tantalum nitride material on a substrate from a precursor composition therefor, including the steps of vaporizing the precursor composition to form a precursor vapor and contacting the precursor vapor with a substrate under deposition conditions to deposit on the substrate the tantalum nitride material, wherein the tantalum nitride precursor composition comprises at least one tantalum amide species selected from the above-described selection group of tantalum compounds and complexes, in a solvent for the tantalum amide species.
The tantalum nitride precursor composition thus may be provided as a liquid composition, which is delivered to a vaporizer to effect vaporization and formation of the tantalum nitride precursor vapor, with the vapor being transported to a deposition zone containing the substrate for the formation of the tantalum nitride material on the substrate. The formation of tantalum nitride material on the substrate may be carried out by a deposition process such as chemical vapor deposition, assisted chemical vapor deposition, ion implantation, molecular beam epitaxy and rapid thermal processing.
Other aspects and features of the invention will be more fully apparent from the ensuing disclosure and appended claims.

DETAILED DESCRIPTION OF THE INVENTION, AND PREFERRED EMBODIMENTS THEREOF

Figure 1:
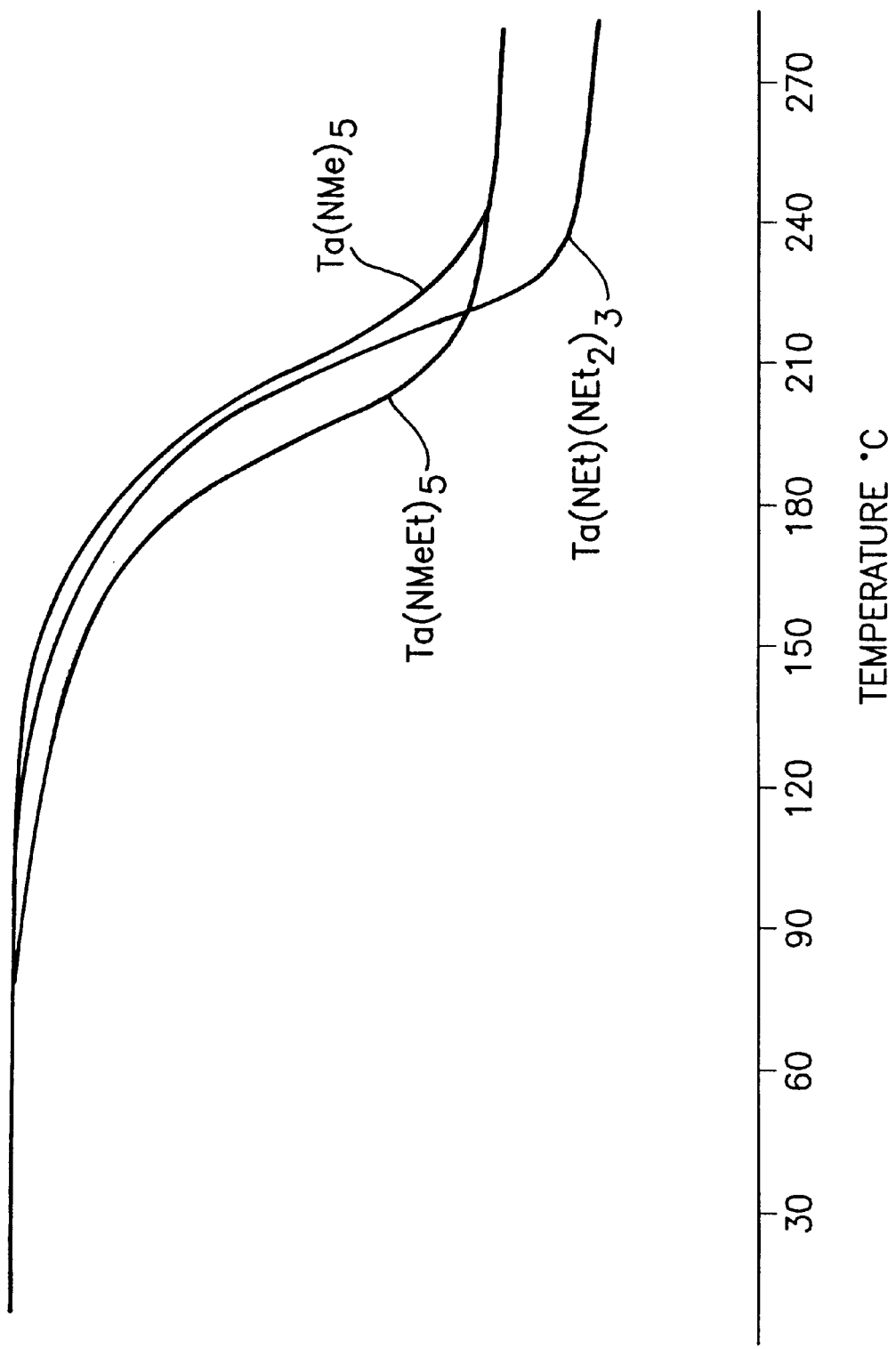
FIG. 1 is a Thermal Gravimetric Analysis (TGA) plot comparing the volatility of Ta(NMeEt)$_5$ with Ta(NEt)(NEt$_2$)$_3$ and Ta(NMe)$_5$.

The present invention is based on the discovery of highly advantageous Ta and Ti source reagents, including Ta source reagents useful for forming Ta-based barrier layers on substrates such as microelectronic device structures for applications such as copper metallization of semiconductor device structures.

The Ta source reagents of the invention include TaN source reagents including Ta amides, as well as single source precursors that are advantageous for the deposition of TaSiN and TiSiN in which silicon is incorporated at the molecular level into the precursor.

In the provision of Ta amide precursors for the formation of TaN barrier layers, useful precursors include tantalum amide precursor compositions comprising at least one tantalum amide species selected from the group consisting of:
(i) tethered amine tantalum complexes of the formula:

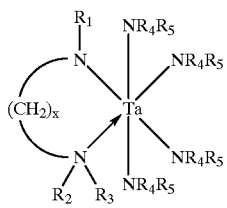

wherein:
  X is 2 or 3;
  each of $R_1$–$R_1$ is independently selected from the group consisting of H, $C_1$–$C_4$ alkyl, aryl (e.g., phenyl), $C_1$–$C_6$ perfluoroalkyl (e.g., a trifluoroalkyl substituent whose alkyl moiety is $C_{1-4}$ alkyl, such as trifluoromethyl), and trimethylsilyl;
(ii) β-diimines of the formula:

wherein:

G is a β-diimino ligand;

each Q is selected from the group consisting of H, $C_1$–$C_6$ alkyl, aryl and $C_1$–$C_6$ perfluoroalkyl; and x is an integer from 1 to 4 inclusive;

(iii) tantalum diamide complexes of the formula $$Ta(N(R_1)(CH_2)_xN(R_2))_y(NR_3R_4)_{5-2y}$$

wherein:

x is 1 or 2;

y is 1 or 2;

each of $R_1$–$R_4$— is independently selected from the group consisting of H, $C_1$–$C_4$ alkyl, aryl, perfluoroalkyl, and trimethylsilyl;

(iv) tantalum amide compounds of the formula $$Ta(NRR')_5$$

wherein each R and R' is independently selected from the group consisting of H, $C_1$–$C_4$ alkyl, phenyl, perfluoroalkyl, and trimethylsilyl, subject to the proviso that in each NRR' group, R R';

(v) β-ketoimines of the formula

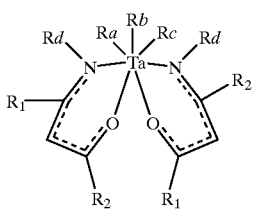

wherein each of $R_1$, $R_2$, $R_a$, $R_b$, $R_c$ and $R_d$ is independently selected from H, aryl, $C_1$–$C_6$ alkyl, and $C_1$–$C_6$ perfluoroalkyl; and (vi) tantalum cyclopentadienyl compounds of the formula

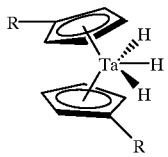

wherein each R is independently selected from the group consisting of H, methyl, ethyl, isopropyl, t-butyl, trimethylsilyl.

For the growth of TaN barrier layers it is desirable that the precursors be free of oxygen so that the formation of tantalum oxide is avoided. Tantalum amides, which have preexisting Ta—N bonds, are therefore attractive precursors. However, homoleptic tantalum amides such as $Ta(NMe_2)_5$ suffer from reduced volatility, due to the bridging of multiple metal centers through the —NMe2 group, analogous to that observed for $Ta(OEt)_5$.

The present invention enhances the volatility of tantalum amides by limiting the degree of intermolecular interactions. To thwart such interactions the use of tethered amine ligands may be employed. For instance, substitution of one of the —NMe2 groups with —N(CH$_3$)(CH$_2$CH$_2$)—NMe$_2$ gives the tantalum amide composition of formula I below, a monomer, with a stable five-membered metallacycle structure. A variety of tethered ligands may be similarly employed. Ligand species of the general formula $R_1N(CH_2)_x NR_2R_3$ where $R_1$, $R_2$, $R_3$ can be independently chosen from H, Me, Et, $^t$Bu, Ph, $^i$Pr, $CF_3$ or $SiMe_3$ groups, appropriately selected to maximize volatility, are preferred. X can be 2 or 3 so that stable 5 or 6 membered chelating rings result.

I

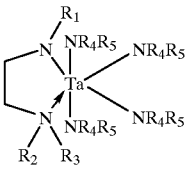

The use of β-diimmines offers alternative precursor compositions that maximize volatility and minimize detrimental exchange reactions. For instance, $Ta(nacnac)(NMe_2)_4$ (directly analogous to $Ta(OiPr)_5(thd)$) is illustrative of precursors of such type that may be usefully employed for the deposition of TaN diffusion barriers. In complexes of the formula $Ta(R_1N—C(R_2)—CH—C(R_3)—N(R_4))_x(NR_5R_6)_{5-x}$, formula (II) below, $R_1$–$R_6$ can each be independently selected from substituent species such as H, Me, Et, $^t$Bu, Ph, $^i$Pr, $SiMe_3$, and $CF_3$.

II

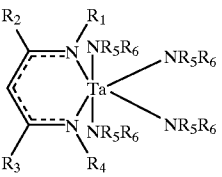

Alternatively, the TaN precursor may utilize diamide ligands such as $N(R_1)(CH_2)_xN(R_2)$ to form mixed ligand complexes such as those of the formula $Ta(N(R_1)(CH_2)_xN(R_2))_x(NR_3R_4)_{5-2x}$, formula (III) below, in, which each of $R_1$–$R_4$ can be independently selected from substituents such as H, Me, Et, $^t$Bu, Ph, $^i$Pr, $SiMe_3$, and $CF_3$ groups.

III

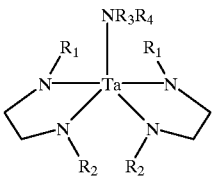

In a simple form, unsymmetrical amides can be employed to thwart intermolecular interactions and disrupt crystal packing forces. Thus, a suitable precursor could be $Ta(NRR')_5$ where R and R' can be any combination of H, Me, Et, $^t$Bu, Ph, $^i$Pr, $SiMe_3$, $CF_3$, Ph, Cy but RR'. As used herein, the term Ph denotes phenyl, and Cy denotes cycloalkyl.

The aforementioned precursors of the present invention provide Ta source reagents that have beneficial volatility characteristics for applications such as chemical vapor deposition, and are easily and economically synthesized. The Ta source reagents of the invention utilize molecular geometries that are controlled by subtle steric effects.

As an example of such subtle steric effects, $Ta(NMe_2)_5$ reportedly possesses a square pyramidal structure and therefore possess a vacant coordination site useful for coordination to other metal centers via a bridging —NMe$_2$ group, analogous to that observed for Ta(OEt)$_5$. Ta(NMe$_2$)$_5$ therefore is a solid and suffers from reduced volatility. Increasing the steric bulk of the ligand by replacement of the —NMe$_2$ by —NEt$_2$ results in a trigonal bipyramidal compound, Ta(NEt$_2$)$_5$, due to the increased steric bulk of the ethyl group compared to the methyl groups in Ta(NMe$_2$)$_5$. Since trigonal bipyramidal compounds have no free coordination site Ta(NEt$_2$)$_5$ is a liquid but it is unstable to heat.

In order to enhance the volatility of the complex by altering the geometry around the metal center to trigonal bipyramidal, without adding undue steric bulk, Ta(NMeEt)$_5$ was synthesized. Ta(NMeEt)$_5$ is:

(i) a liquid.

(ii) more volatile than Ta(NMe$_2$)$_5$ or Ta(NEt)(NEt$_2$)$_3$ (see FIG. 1).

Figure 2:
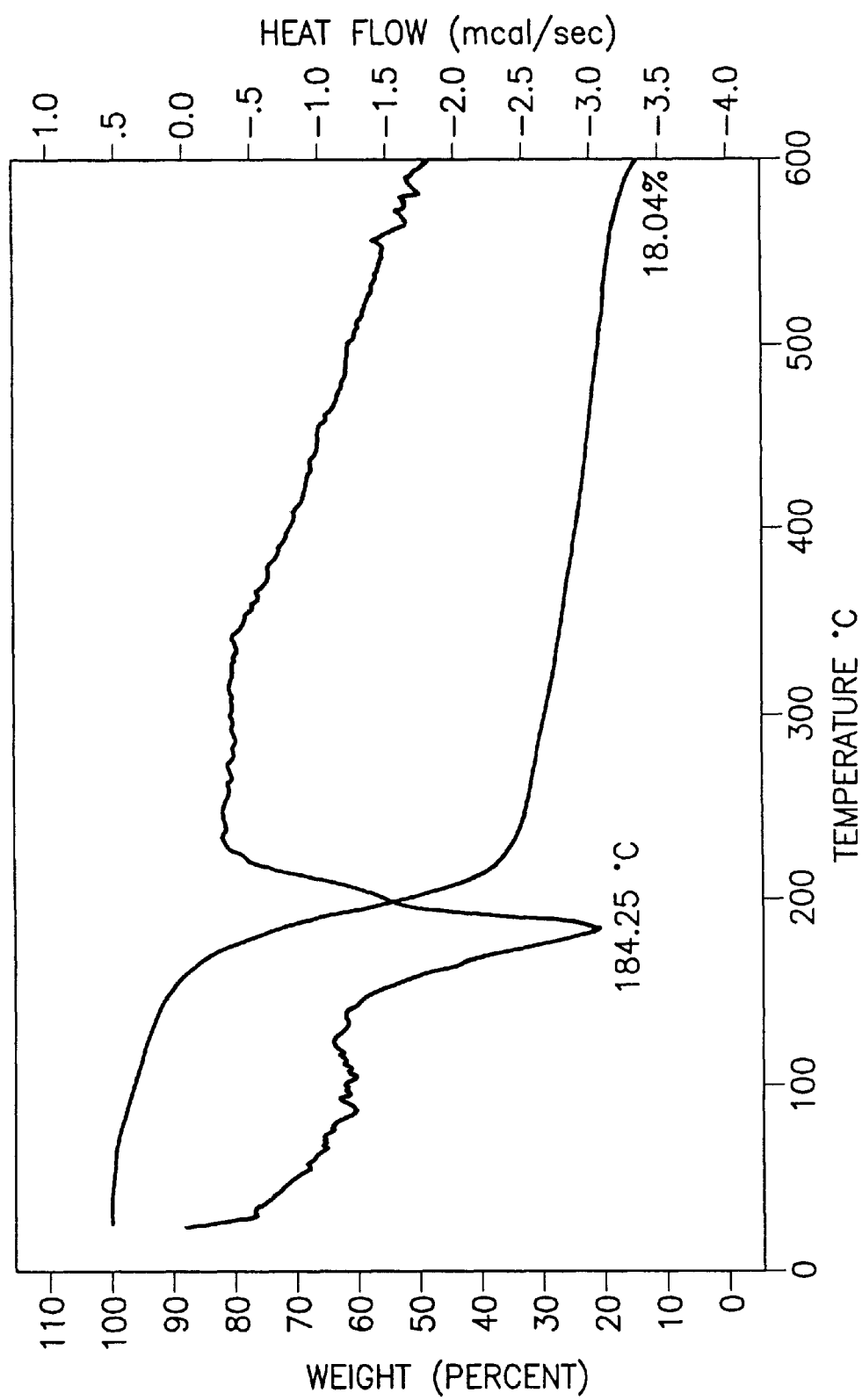
FIG. 2 is an STA plot of Ta(NMeEt)$_5$.

(iii) stable to heat up to its boiling temperature (see FIG. 2).

These properties make Ta(NMeEt)$_5$ a highly desirable precursor for CVD that is superior to the prior art, as shown in FIG. 1, which is a thermal gravimetric analysis (TGA) plot comparing the volatility of Ta(NMeEt)$_5$ vs. Ta(NEt)(NEt$_2$)$_3$ and Ta(Me)$_5$.

FIG. 2 shows an STA plot of Ta(NMeEt)$_5$. Note there is no event in the differential scanning calorimetry (DSC) curve prior to boiling, indicating stability to decomposition.

Figure 3B:
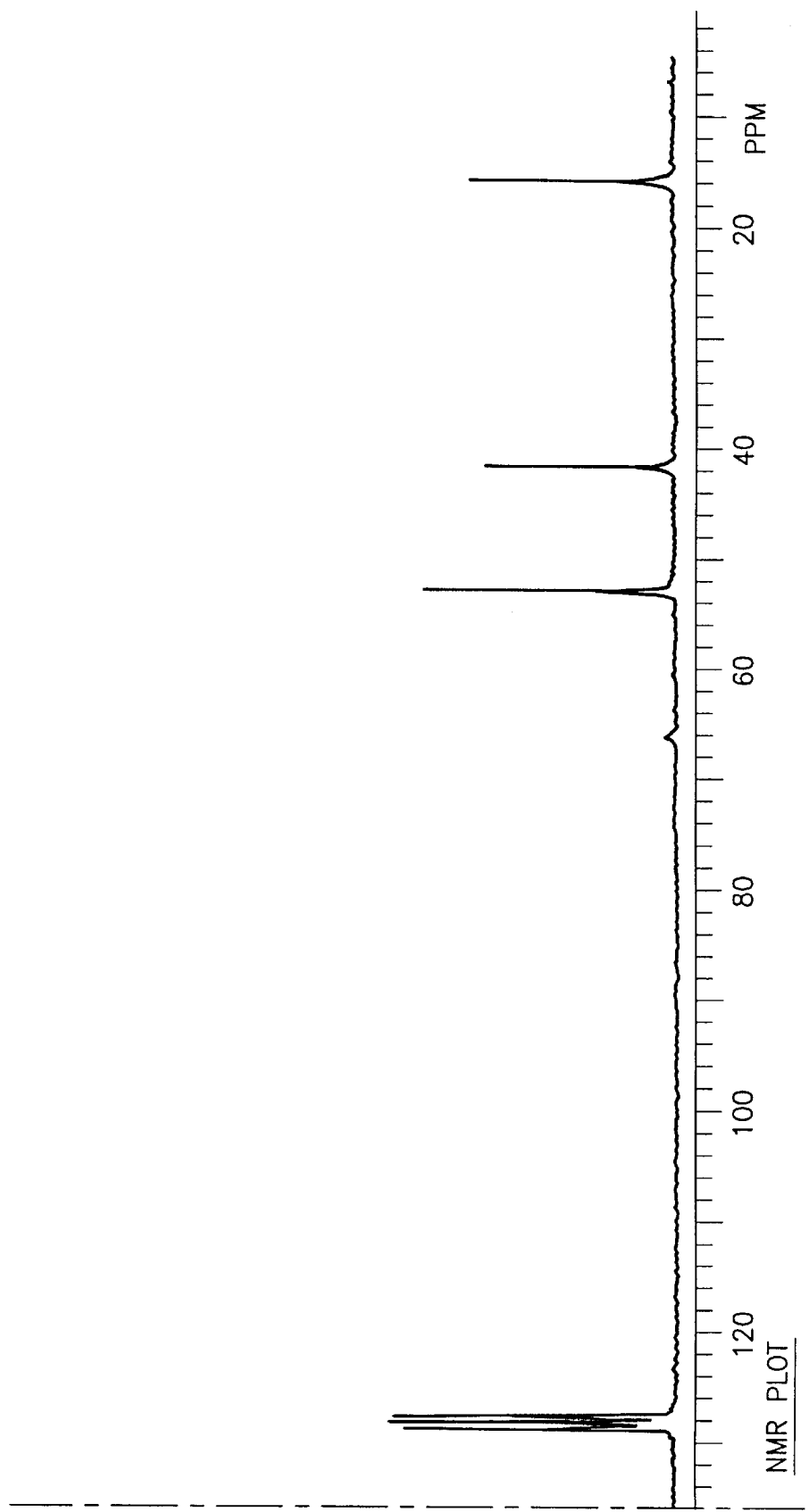
FIG. 3 is a $^1$H and $^{13}$C NMR plot for Ta(NMeEt)$_5$ showing five equivalent amide groups.

FIG. 3 shows an $^1$H and $^{13}$C NMR plot of Ta(NMeEt)$_5$ showing five equivalent amide groups.

In the Ta amide precursors of the invention, the Ta substituents preferably include substituents having slightly increased steric size than —NMe$_2$. Such Ta amide precursors include compounds of the general formula Ta(NR$_1$R$_2$)$_5$, wherein R$_1$ and R$_2$ are independently selected from substituents such as —H, —Me, —Et, —CH$_2$CH(Me)—, —CF$_3$, —$^t$Bu, —$^i$Pr, and SiMe$_3$.

In the broad practice of the present invention, other compounds of the general formula Ta(NR$_1$R$_2$)$_3$(NR$_2$R$_3$)$_2$ can also be optimized for volatility and stability. In such precursor compositions, the steric size of —NR$_1$R$_2$>—NR$_2$R$_3$ so that the more bulky —NR$_1$R$_2$ group occupies the axial position and the —NR$_2$R$_3$ group occupies the more sterically crowded equatorial position. In these compositions, R$_{14}$ can be selected from any combination of —H, —Me, —Et, —CH$_2$CH(Me)—, —CF$_3$, —$^t$Bu, —$^i$Pr, and —SiMe$_3$.

The deposition of Ta metal in accordance with the process of the present invention may be carried out with a wide variety of precursor materials of the types disclosed herein. In some cases, it may be detrimental to have an oxygen containing ligand present in the molecule which could ultimately result in Ta$_2$O$_3$ formation. In such instances, the use of β-ketoimine or β-diimine ligands, such as those described below, enables highly efficient chemical vapor deposition of TaN and Ta metal.

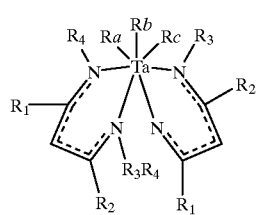

I

In compound I, R$_1$, R$_2$, R$_3$ and R$_4$ may be alike or different and are independently selected from substituents such as H, aryl, C$_{1-6}$ alkyl, and C$_1$–C$_6$ perfluoroakyl. In a specific embodiment, R$_3$ will most likely be H, aryl, C$_1$–C$_6$ alkyl, or C$_1$–C$_6$ perfluoroalkyl. Alternatively, R$_1$ or R$_2$ may be identical to R$_3$. R$_a$, R$_b$, and R$_c$ may be alike or different and are independently selected from the group consisting of H, aryl, C$_1$–C$_6$ alkyl, or C$_1$–C$_6$ perfluoroalkyl.

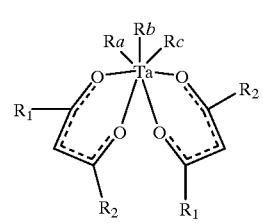

II

In compound II, R$_1$ and R$_2$ may have the same restrictions as discussed above for compound I. R$_a$, R$_b$, and R$_c$, may be equal or different and can be H, aryl, perfluoroaryl, C$_1$–C$_6$ alkyl, or C$_1$–C$_6$ perfluoroalkyl.

Various trimethyl tantalum bis(B-diketonate) complexes may be employed as useful Ta precursors in the broad practice of the invention. For example, Me$_3$Ta(acac)$_2$ has a melting point of 83° C., Me$_3$Ta(tfac)$_2$ has a melting point of 107° C. and Me$_3$Ta(hfac)$_2$ has a melting point of 109° C. The volatility generally increases in the same order with increasing fluorine substitution. These types of materials are potentially usefully employed for Ta film growth in the presence of hydrogen, forming gas or other reducing species. They may also be usefully employed for oxide formation, as for example in CVD of SrBi$_2$Ta$_2$O$_9$.

A third class of materials that is potentially usefully employed for the deposition of Ta metal or TaN films has a hydride precursor structure, as depicted in compound III below. Such compositions have not previously been used for Ta or TaN film growth.

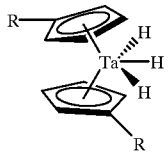

III Bis(cyclopentadienyl)tantalum(V)trihydride

The structure of this Ta precursor may be altered to enhance thermal stability, volatility or physical properties and to achieve the desired film properties, namely high purity and low resistivity. Potential substituents where R on the cyclopentadienyl moiety is varied include R=H, Me, Et, i-Pr, t-Bu, TMSi, etc. in which the substituent is selected to modify the precursor properties. This general class of materials is well-suited for Ta film growth especially in the presence of H$_2$ or forming gas.

In use, the precursors of the invention may be employed in a neat liquid form, or alternatively they may be utilized in solution or suspension form, in which the precursor is mixed, blended or suspended in a compatible liquid solvent such as a solvent composition of the type disclosed in U.S. application Ser. No. 08/414,504 filed Mar. 31, 1995, in the names of Robin A. Gardiner, Peter S. Kirlin, Thomas H. Baum, Douglas Gordon, Timothy E. Glassman, Sofia Pombrik, and Brian A. Vaartstra, the disclosure of which is hereby incorporated herein by reference in its entirety.

The solvent may for example be selected from the group consisting of C$_6$–C$_{10}$ alkanes, C$_6$–C$_{10}$ aromatics, and compatible mixtures thereof. Illustrative alkane species include hexane, heptane, octane, nonane and decane. Preferred alkane solvent species include $C_8$ and $C_{10}$ alkanes. Preferred aromatic solvent species include toluene and xylene.

The present invention also contemplates various single source precursors for the formation of TaSiN and TiSiN layers on substrates. Two general variant approaches can be used for the provision of single source precursors that are advantageous for the deposition of TaSiN and TiSiN. These approaches are:

(1) use of silyl amides as precursors; and
(2) provision of direct metal-silicon bonds in the precursors.

Metal silylamides represent the most direct and cost-effective method for the introduction of silicon into the product film formed by the precursor. Examples include the clean formation of $Bi_{12}SiO_{20}$ upon heating $Bi(NSiMe_3)_3$ in oxygen. For the deposition of TaSiN and TiSiN suitable precursors include those of the general formula:

$$Ta(NR_1R_2)_x(NR_3R_4)_{5-x}/Ti(NR_1R_2)_x(NR_3R_4)_{4-x}$$

or $$Ta(NR_1)(NR_2R_3)_3$$

where each of $R_1$, $R_2$, $R_3$ and $R_4$ are independently selected from the group consisting of H, $C_1$–$C_8$ alkyl (e.g., Me, Et, $^tBu$, $^iPr$, etc.), aryl (e.g., phenyl), $C_1$–$C_8$ perfluoroalkyl (e.g., $CF_3$ or a fluoroalkyl whose alkyl moiety is $C_1$–$C_4$, such as trifluoromethyl), or a silicon-containing group such as silane ($SiH_3$), alkylsilane, (e.g., $SiMe_3$, $Si(Et)_3$, $Si(^iPr)_3$, $Si(^tBu)_3$, perfluoroalkylsilyl (e.g., $Si(CF_3)_3$), triarylsilane (e.g., $Si(Ph)_3$), or alkylsilylsilane (e.g., $Si(SiMe_3)_x(Me)_{3-x}$). The number of silicon-containing R groups can be used as an independent variable to control the amount of silicon in the film. For precursors of the type $Ta(NR_1)(NR_2R_3)_3$ the location of the R group (i.e., imide vs. amide) will also determine the incorporation efficiency of silicon into the film.

Precursors containing preexisting metal to silicon bonds are potentially highly effective for the deposition of TaSiN/TiSiN. Useful precursors have the general formula:

$$Ta(SiR_1R_2R_3)_x(NR_4R_5)_{5-x}/Ti(SiR_1R_2R_3)_x(NR_4R_5)_{4-x}$$

where $R_{1-5}$ can any be combination of H, Me, Et, $^tBu$, Ph, $^iPr$, $CF_3$, $SiH_3$, $SiMe_3$, $Si(CF_3)_3$, $Si(Et)_3$, $Si(^iPr)_3$, $Si(^tBu)_3$, $Si(Ph)_3$, $Si(SiMe_3)_x(Me)_{3-x}$. Two illustrative titanium amides with metal to silicon bonds are $Ti(Si(SiMe_3)_3)(NMe_2)_3$ and $Ti(Si(SiMe_3)_3)(NEt_2)_3$.

Another class of useful precursors are complexes where one of the amide or silyl groups has been replaced by a cyclopentadiene or substituted cyclopentadiene. These precursors have the general formula;

$$(Cp'')Ta(SiR_1R_2R_3)_x(NR_4R_5)_{4-x}/(Cp'')_2Ti(SiR_1R_2R_3)(NR_4R_5)$$

where, once again, $R_{1-5}$ can any be combination of H, Me, Et, $^tBu$, Ph, $^iPr$, $CF_3$, $SiH_3$, $SiMe_3$, $Si(CF_3)_3$, $Si(Et)_3$, $Si(^iPr)_3$, $Si(^tBu)_3$, $Si(Ph)_3$, $Si(SiMe_3)_x(Me)_{3-x}$ and $Cp''$ is $C_5H_xMe_{(5-x)}$ (where x–0–5). Cyclopentadienyl complexes of Ta and Ti containing direct metal to silicon bonds have not heretofore been used or considered for formation of TaN, TiN, TaSiN or TiSiN films.

For liquid delivery CVD of Ta- or Ti-based films or coatings on a substrate, the corresponding source reagent may be provided as a liquid starting material which then is vaporized to form the precursor vapor for the chemical vapor deposition process.

The vaporization may be carried out by injection of the liquid in fine jet, mist or droplet form into a hot zone at an appropriate temperature for vaporization of the source reagent liquid. Such injection may be carried out with a nebulization or atomization apparatus of conventional character, producing a dispersion of finely divided liquid particles, e.g., sub-micron to millimeter diameter scale. The dispersed liquid particles may be directed at a substrate at a sufficiently high temperature to decompose the source reagent and produce a coating of the Ta- or Ti-based material product on the substrate.

Alternatively, the liquid may be dispensed from a suitable supply vessel of same, onto a heated element, such as a screen, grid or other porous or foraminous structure, which is heated to a sufficiently high temperature to cause the liquid to flash volatilize into the vapor phase, as for example in the manner described in U.S. Pat. No. 5,204,314 to Peter S. Kirlin, et al. and U.S. Pat. No. 5,711,816 to Peter S. Kirlin, et al., the disclosures of which hereby are incorporated herein by reference in their entirety.

Regardless of the manner of volatilization of the source reagent, the vapor thereof is flowed to contact the substrate on which the Ta-based or Ti-based material is to be deposited, at appropriate deposition conditions therefor, which may be readily determined within the skill of the art, by the expedient of varying the process conditions (temperature, pressure, flow rate, etc.) and assessing the character and suitability of the resulting deposited material.

As an alternative to the use of the source reagent in a neat liquid form, the source reagent may be dissolved or mixed into a compatible solvent medium which does not preclude the efficacy of the resulting composition for CVD usage. For example, the source reagent may be utilized in a solvent composition of the type disclosed in the aforementioned U.S. application Ser. No. 08/414,504 filed Mar. 31, 1995, in the names of Robin A. Gardiner, et al. The resulting solution or suspension of the source reagent and solvent medium may then be injected, dispersed, flash vaporized, or otherwise volatilized in any suitable manner, as for example by the techniques described above in connection with the use of the neat liquid source reagent.

While the invention has been described illustratively herein with respect to specific features, aspects and embodiments thereof, it is to be appreciated that the utility of the invention is not thus limited, but rather extends to and encompasses other applications, aspects, features and embodiments, such as will readily suggest themselves to those of ordinary skill in the art. The invention is therefore to be broadly construed and interpreted, in reference to the ensuing claims.

What is claimed is:

1. A method of forming Ta or Ti material on a substrate from a precursor, comprising vaporizing said precursor to form a precursor vapor, and contacting the precursor vapor with the substrate to form said Ta or Ti material thereon, wherein the precursor comprises at least one tantalum and/or titanium species selected from the group consisting of:

(i) tethered amine tantalum complexes of the formula:

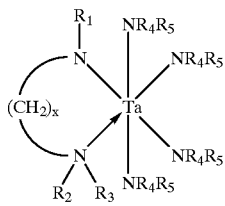

wherein:

x is 2 or 3;

each of $R_1$–$R_5$ is independently selected from the group consisting of H, $C_1$–$C_4$ alkyl, aryl, $C_1$–$C_6$ perfluoroalkyl and trimethylsilyl;

(ii) β-diimines of the formula:

$$TaG_xQ_{5-x}$$

wherein:

G is a β-diimino ligand;

each Q is selected from the group consisting of H, $C_1$–$C_6$ alkyl, aryl and $C_1$–$C_6$ perfluoroalkyl; and x is an integer from 1 to 4 inclusive;

(iii) tantalum diamide complexes of the formula $$Ta(N(R_1)(CH_2)_xN(R_2))_y(NR_3R_4)_{5-2}$$

wherein:

x is the integer 1 or 2;

y is the integer 1 or 2;

each of $R_1$–$R_4$ is independently selected from the group consisting of H, $C_1$–$C_4$ alkyl, aryl, perfluoroalkyl, and trimethylsilyl;

(iv) tantalum amide compounds of the formula $$Ta(NRR')_5$$

wherein each R and R' is independently selected from the group consisting of H, $C_1$–$C_4$ alkyl, phenyl, perfluoroalkyl, and trimethylsilyl, subject to the proviso that in each NRR' group, R≠R';

(v) β-ketoimines of the formula

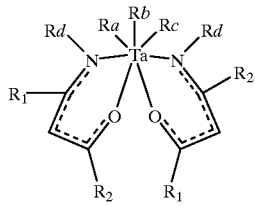

wherein each of $R_1$, $R_2$, $R_a$, $R_b$, $R_c$ and $R_d$ is independently selected from H, aryl, $C_1$–$C_6$ alkyl, and $C_1$–$C_6$ perfluoroalkyl; and (vi) tantalum cyclopentadienyl compounds of the formula

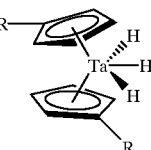

wherein each R is trimethylsilyl;

(vii) $Ta(NR_1R_2)_x(NR_3R_4)_{5-x}/Ti(NR_1R_2)_y(NR_3R_4)_{4-y}$ wherein each of $R_1$, $R_2$, $R_3$ and $R_4$ are independently selected from the group consisting of H, $C_1$–$C_8$ alkyl aryl, $C_1$–$C_8$ perfluoroalkyl or a silicon-containing group selected from the group consisting of silane, alkylsilane, perfluoroalkylsilyl, triarylsilane and alkylsilylsilane, wherein x is an integer from 1 to 5 inclusive; and y is an integer from 1 to 4 inclusive;

(viii) $Ta(NR_1)(NR_2R_3)_3$ wherein each of $R_1$, $R_2$, and $R_3$ are independently selected from the group consisting of H, $C_1$–$C_8$ alkyl aryl, $C_1$–$C_8$ perfluoroalkyl or a silicon-containing group selected from the group consisting of silane, alkylsilane, perfluoroalkylsilyl, triarylsilane and alkylsilylsilane, with the proviso that $R_1 \neq C_3$–$C_5$ alkyl group when $R_2=R_3=E_t$ (ix) $Ta(SiR_1R_2R_3)_x(NR_4R_5)_{5-x}/Ti(SiR_1R_2R_3)_y(NR_4R_5)_{4-y}$ wherein each of $R_{1-5}$ is independently selected from the group consisting of H, Me, Et, $^tBu$, Ph, $^iPr$, $CF_3$, $SiH_3$, $SiMe_3$, $Si(CF_3)_3$, $Si(Et)_3$, $Si(^iPr)_3$, $Si(^tBu)_3$, $Si(Ph)_3$, and $Si(SiMe_3)_z(Me)_{3-z}$, wherein x is an integer from 1 to 4 inclusive; y is an integer from 1 to 3 inclusive; and z is an integer from 1 to 3 inclusive; and (x) $(Cp'')Ta(SiR_1R_2R_3)_x(NR_4R_5)_{4-x}/(Cp'')_2Ti(SiR_1R_2R_3)(NR_4R_5)$ wherein each of $R_{1-5}$ is independently selected from the group consisting of H, Me, Et, $^tBu$, Ph, $^iPr$, $CF_3$, $SiH_3$, $SiMe_3$, $Si(CF_3)_3$, $Si(Et)_3$, $Si(^iPr)_3$, $Si(^tBu)_3$, $Si(Ph)_3$, $Si(SiMe_3)_y(Me)_{3-y}$ and Cp'' is $C_5H_zMe_{(5-z)}$, wherein x is an integer from 1 to 3 inclusive; y is an integer from 1 to 3 inclusive; and z is an integer from 0 to 5 inclusive.

2. The method according to claim 1, of forming Ta material on said substrate from said precursor, wherein said precursor is a tantalum species selected from the group consisting of tantalum species (i), (ii), (iii), (iv), (v) and (vi), and wherein said Ta material is TaN.

3. A method according to claim 1, further comprising a solvent for said precursor.

4. A method according to claim 3, wherein said solvent is selected from the group consisting of $C_6$–$C_{10}$ alkanes, $C_6$–$C_{10}$ aromatics, and compatible mixtures thereof.

5. A method according to claim 3, wherein said solvent is selected from the group consisting of hexane, heptane, octane, nonane, decane, toluene and xylene.

6. A method according to claim 1, comprising liquid delivery chemical vapor deposition of said precursor.

7. A method according to claim 1, comprising deposition of Ta and/or Ti on said substrate by a technique selected from the group consisting of chemical vapor deposition, assisted chemical vapor deposition, ion implantation, molecular beam epitaxy and rapid thermal processing.

8. A method according to claim 1, wherein the substrate comprises a microelectronic device structure.

9. A method according to claim 8, wherein TaN or TaSiN is deposited on said substrate, and the substrate thereafter is metallized with copper or integrated with a ferroelectric thin film.

10. A method according to claim 8, wherein TaN is deposited on said substrate, and the substrate thereafter is metallized with copper or integrated with a ferroelectric thin film.

11. A method according to claim 1, comprising liquid delivery chemical vapor deposition of said precursor to form TaN on the substrate, and thereafter metallizing the substrate with copper or integrating the substrate with a ferroelectric thin film.

12. A method according to claim 1, wherein the precursor comprises pentakis(N-methyl, N-ethyl amido)tantalum.

13. A method of depositing a tantalum-containing film on a substrate, comprising vaporizing a precursor composition comprising pentakis(N-methyl, N-ethylamido)tantalum to form a precursor vapor, and contacting said vapor with the substrate to deposit said tantalum-containing film on the substrate.

14. A method according to claim 13, wherein the vaporizing and contacting steps comprise liquid delivery chemical vapor deposition.

15. A method of fabricating a microelectronic device structure, comprising vaporizing a precursor composition comprising pentakis(N-methyl, N-ethylamido)tantalum to form a precursor vapor, and contacting said vapor with a substrate to deposit a tantalum-containing film on the substrate, and thereafter metallizing the substrate with copper or integrating it with a ferroelectric thin film.

16. A method of claim 15, wherein the tantalum-containing film comprises tantalum nitride.

* * * * *

UNITED STATES PATENT AND TRADEMARK OFFICE
CERTIFICATE OF CORRECTION

PATENT NO. : 6,379,748 B1
DATED : April 30, 2002
INVENTOR(S) : Gautam Bhandar et al.

It is certified that error appears in the above-identified patent and that said Letters Patent is hereby corrected as shown below:

Column 4,
Line 1, replace "(v)" with -- (vi) --;
Line 28, after "Si(Ph)$_3$" delete "Si(SiMe$_3$)$_x$(Me)$_{3-x}$"
Line 30, replace "(ix)" with the following:
-- (ix)   (Cp$^n$)Ta(SiR$_1$R$_2$R$_3$)$_x$(NR$_4$R$_5$)$_{4-x}$ / (Cp$^n$)$_2$Ti(SiR$_1$R$_2$R$_3$)(NR$_4$R$_5$) --;
Line 31, replace "can any be" with -- can be any --;

Column 9,
Line 41, after "compositions," delete "R$_{14}$" and substitute -- R$_{1-4}$ --;

Column 13,
Line 34, cancel the formula and substitute:
-- Ta(N(R$_1$)(CH$_2$)$_x$N(R$_2$))$_y$(NR$_3$R$_4$)$_{5-2y}$ --;

Column 14,
Line 14, after "alkyl" insert a -- , -- (comma);
Line 22, after "alkyl" insert a -- , -- (comma).

Signed and Sealed this

Twenty-eighth Day of December, 2004

JON W. DUDAS
*Director of the United States Patent and Trademark Office*